United States Patent [19]

Nakamura et al.

[11] Patent Number: 5,770,221
[45] Date of Patent: Jun. 23, 1998

[54] FORMULATION FOR PERCUTANEOUS ADMINISTRATION FOR TREATING DISTURBANCE IN MICTURITION

[75] Inventors: Katsuhiro Nakamura; Nobuyuki Koga, both of Tsukuba, Japan

[73] Assignee: Hisamitsu Pharmaceutical Co., Inc., Saga, Japan

[21] Appl. No.: 737,160

[22] PCT Filed: May 18, 1995

[86] PCT No.: PCT/JP95/00946

§ 371 Date: Nov. 15, 1996

§ 102(e) Date: Nov. 15, 1996

[87] PCT Pub. No.: WO95/31190

PCT Pub. Date: Nov. 23, 1995

[30] Foreign Application Priority Data

May 18, 1994 [JP] Japan ..................... 6-128162

[51] Int. Cl.⁶ .............. A61K 9/70; A61K 47/32; A61M 37/00
[52] U.S. Cl. .............. 424/449; 424/448; 424/486; 604/307; 514/772.4
[58] Field of Search ............... 424/484, 486, 424/448, 449

[56] References Cited

U.S. PATENT DOCUMENTS

| | | | |
|---|---|---|---|
| 4,262,003 | 4/1981 | Urquhart et al. | 424/267 |
| 4,623,346 | 11/1986 | von Bittera et al. | 424/449 |
| 4,793,337 | 12/1988 | Freeman et al. | 128/156 |
| 4,938,759 | 7/1990 | Enscore et al. | 424/449 |
| 5,059,189 | 10/1991 | Cilento et al. | 424/449 |
| 5,411,740 | 5/1995 | Lee et al. | |
| 5,480,648 | 1/1996 | Wendel et al. | 424/449 |
| 5,503,843 | 4/1996 | Santus et al. | |
| 5,508,038 | 4/1996 | Wang et al. | 424/448 |

FOREIGN PATENT DOCUMENTS

| | | |
|---|---|---|
| 61-271219 | 1/1986 | Japan . |
| 4-95023 | 3/1992 | Japan . |
| 4-99720 | 3/1992 | Japan . |
| 4266821 | 9/1992 | Japan . |
| 4273818 | 9/1992 | Japan . |

*Primary Examiner*—Edward J. Webman
*Attorney, Agent, or Firm*—Townsend & Banta

[57] ABSTRACT

A formulation for percutaneous administration for treating disturbance in micturition, which comprises a medicine for treating disturbance in micturition contained in an adhesive layer containing a low-molecular weight polyisobutylene, a high-molecular weight polyisobutylene and an oil as main bases is disclosed. A formulation for percutaneous administration for treating disturbance in micturition, which comprises a medicine for treating disturbance in micturition contained in an adhesive containing a low-molecular weight polyisobutylene, a high-molecular weight polyisobutylene, an oil and an styrene-isoprene-styrene block copolymer as main bases is also disclosed. The formulation for percutaneous administration for treating disturbance in micturition of the present invention is excellent in stability against change with time, low irritative to skin, and excellent in transdermal absorbability, by using these specified base components.

8 Claims, 3 Drawing Sheets

FORMULATION FOR PERCUTANEOUS ADMINISTRATION FOR TREATING DISTURBANCE IN MICTURITION

TECHNICAL FIELD

The present invention relates to a formulation for percutaneous administration for treating disturbance in micturition. More particularly, the present invention relates to a formulation for percutaneous administration effective for treating disturbance in micturition, such as urinary incontinence, difficulty of micturition, pollakisuria, pain on micturition and the like.

BACKGROUND ART

The disturbance in micturition is a generic term concerning the disorders of micturition conduct, and it includes urinary incontinence, difficulty of micturition, pollakisuria, pain on micturition and the like.

Among them, the urinary incontinence is a disorder of micturition which may be occurred in any age groups, and it has been increasingly given attention by the general public in recent years. In particular, the incidence of urinary incontinence in aged people is very high, it has been still increasing, and it becomes a big problem before the coming aged people society. Moreover, without regard to whether aged or not, there are very many women suffering from urinary incontinence, and thus it can not be overlooked.

There have been many attempts to treat the disturbances in micturition such as urinary incontinence, and many peroral-administration type medicine for treating disturbance in micturition have already been on the market.

However, since the patients suffering from severe cerebrovascular disease bringing disturbance in micturition or the patients after operations of various tumors and the like, need times when they are bedridden, the administrations of the peroral-type medicine which must be administered every constant hours, are difficult in many cases.

On the other hand, in order to avoid the extreme decrease in bioavailability due to the so-called "first-pass effect" of liver in the case of the peroral administration of medicines, and in order to prevent the increase in incidence of side-effects due to the temporary increase in the concentration in blood, there have been many attempts to form various medicines into formulation for percutaneous administration as a method for slow-releasing medicines. The medicine for treating disturbance in micturition is expected to be administered as a formulation for percutaneous administration.

The Japanese Un-examined Patent Publication No.Hei 4-266821 describes that the medicines for treating disturbance in micturition such as terodiline, oxybutynin, propiverine, flavoxate are formed into percutaneous absorption-type therapeutic formulations.

In addition, the Japanese Un-examined Patent Publication No.Hei 4-273818 describes that terodiline, oxybutynin and the like are formed into percutaneous absorption-type therapeutic formulations such as patches and solutions.

However, in these publications, the drug stability which is important in forming formulations, and the physical stability, the irritativeness to skin and the constant releasability of the formulations are not sufficiently investigated. For example, although in Examples in the above Japanese Un-examined Patent Publication No.Hei 4-266821, terodiline and oxybutynin are used as hydrochlorides, and aqueous bases are prepared to be investigated, a sufficient drug stability can not be expected due to the mutual action of many additives and water contained in the formulation. The number of times of application of drugs is expected to be small, such as one time/day or one time/two days, by the above reasons and the like. However, in the case of aqueous bases, the number of times of application need to be large, because the adhesive stability at the time of long period adhesion is poor.

Further, it is the same in the above Japanese Un-Examined Patent Publication No.Hei 4-273718, the stability of drug and the irritativeness to skin and the like of the formulation are poor, and it can not be deemed that the formulation meets the requirements of commercialization.

Therefore, the purpose of the invention is to provide a formulation for percutaneous administration for treating disturbance in micturition, which can stably maintain a medicine for treating disturbance in micturition being an active component, and by which the medicine may be percutaneously absorbed constantly and efficiently and an excellent pharmaceutical effect is exhibited.

The present inventors have researched earnestly, and as the results, they found that the above-mentioned purpose may be attained by containing a medicine for treating disturbance in micturition into an adhesive which contains a low-molecular weight polyisobutylene, a high-molecular weight polyisobutylene and an oil as main bases.

DISCLOSURE OF INVENTION

The present invention relates to a formulation for percutaneous administration for treating disturbance in micturition, which comprises a medicine for treating disturbance in micturition contained in an adhesive containing a low-molecular weight polyisobutylene, a high-molecular weight polyisobutylene and an oil as main bases.

The present invention also relates to the formulation for percutaneous administration for treating disturbance in micturition, which comprises, based on the total amount of the adhesive, 0.01 to 50 parts by weight of the medicine for treating disturbance in micturition contained in the adhesive containing 1 to 60 parts by weight of the low-molecular weight polyisobutylene, 0.1 to 40 parts by weight of the high-molecular weight polyisobutylene and 10 to 60 parts by weight of the oil as main bases.

The present invention also relates to a formulation for percutaneous administration for treating disturbance in micturition, which comprises a medicine for treating disturbance in micturition contained in an adhesive containing a low-molecular weight polyisobutylene, a high-molecular weight polyisobutylene, an oil and an styrene-isoprene-styrene block copolymer as main bases.

The present invention also relates to the formulation for percutaneous administration for treating disturbance in micturition, which comprises, based on the total amount of the adhesive, 0.01 to 50 parts by weight of the medicine for treating disturbance in micturition contained in the adhesive containing 1 to 60 parts by weight of the low-molecular weight polyisobutylene, 0.1 to 40 parts by weight of the high-molecular weight polyisobutylene, 10 to 60 parts by weight of the oil and 5 to 50 parts by weight of the styrene-isoprene-styrene block copolymer as main bases.

The present invention also relates to the formulation for percutaneous administration for treating disturbance in micturition, wherein the medicine for treating disturbance in micturition is a medicine for treating urinary incontinence, a medicine for treating difficulty of micturition, a medicine for treating pollakisuria, or a medicine for treating pain on micturition.

The present invention also relates to the formulation for percutaneous administration for treating disturbance in micturition, wherein the medicine for treating disturbance in micturition is a medicine for treating urinary incontinence.

The present invention also relates to the formulation for percutaneous administration for treating disturbance in micturition, wherein the viscosity-average molecular weight of the low-molecular weight polyisobutylene is in the range from 10,000 to 100,000 and the viscosity-average molecular weight of the high-molecular weight polyisobutylene is in the range from 500,000 to 2,500,000.

The present invention also relates to the formulation for percutaneous administration for treating disturbance in micturition, wherein the oil is at least one selected from the group comprising liquid paraffin having a viscosity of 5 to 100 $mm^2/s$, natural and synthetic squalene and squalane.

The present invention also relates to the formulation for percutaneous administration for treating disturbance in micturition, which further comprises a transdermal absorption enhancer.

The present invention will be explained in detail.

The medicine for treating disturbance in micturition which is an active component of the formulation for percutaneous administration for treating disturbance in micturition, is not limited to, but may be classified into the medicines for treating urinary incontinence, the medicines for treating difficulty of micturition, the medicines for treating pollakisuria or the medicines for treating pain on micturition.

The term "urinary incontinence" used in the invention means involuntary defluxion of urine, and may include the overflow type incontinence which is occurred when bladder is filled with urine anuretically and urine is overflowed, the urgent type incontinence which is occurred for the reason that the micturition can not be controlled when micturition is felt, the stress type incontinence which is occurred only when the abdominal pressure is increased, the true type incontinence which is occurred continuously for the reason that the bladder is not filled with urine due to the loss of function of sphincter muscle of urethra and the like.

The term "difficulty of micturition" means a condition when urine can not easily voided, and may include the delay of starting of micturition, the extension of micturition time, the impossibility of micturition without applying abdominal pressure, the fining of ureter, the dropping of urine at the end of micturition and the like.

The term "pollakisurea" means a increase of the number of micturition times, and indicates the condition in which approximately 10 or more times/day of micturition is occurred. When the pollakisurea becomes severe, the micturition is not disappeared just after micturition and the tenesmus is occurred. There is the nocturnal micturition in which two or more micturitions are occurred during sleeping.

The term "pain on micturition" means a pain felt in urethra at the time of micturition. The pain may felt only at the beginning or end of micturition in some cases. In addition, there is a pain felt in bladder when bladder is filled.

Further, the medicine for treating disturbance in micturition which is the active component of the formulation for percutaneous administration for treating disturbance in micturition of the present invention, can be classified into 1) the medicines for promoting the contraction of micturition muscle, 2) the medicines for inhibiting the contraction of micturition muscle, 3) the medicines for promoting the tension of sphincter muscle, and 4) the medicines for inhibiting the contraction of sphincter muscle.

As the above 1) medicines for promoting the contraction of micturition muscle, the cholinergic agents, the anticholinesterase agents, the prostaglandins and the like may be exemplified. Further, as the above 2) medicines for inhibiting the contraction of micturition muscle, the anticholinergic agents, the smooth muscle relaxants, the tricyclic antidepressants and the like may be exemplified. Further, as the above 3) medicines for promoting the tension of sphincter muscle, the adrenergic agents and the like may be exemplified. Further, as the above 4) medicines for inhibiting the contraction of sphincter muscle, α-adrenoceptor blockers, the skeletal muscle relaxants and the like may be exemplified.

As the concrete examples of the medicines for treating disturbance in micturition, bethanechol, distigmine, prostaglandins ($PGE_1$, $PGE_2$, $PGF_2\alpha$ et al), propanthelin, oxybutynin, terodiline, flavoxate, propiverine, vamicamide, urapidil, tiropramide, alfuzosin, imipramine, amitriptyne, ethylphenylephrine, ephedrine, phenoxybenzamine, prazosin, bunazocin, diazepam, dantrolene, clenbuterol, terazosin, inaperisone, terflavoxate, naftopidil and the like, or pharmaceutically acceptable salts thereof may be exemplified. Among the pharmaceutically acceptable salts, hydrochloride is particularly preferable.

The medicine for treating disturbance in micturition which is an active component of the formulation for percutaneous administration for treating disturbance in micturition, is desirably contained in the range from 0.01 to 50 parts by weight, preferably in the range from 0.1 to 30 parts by weight, and more preferably in the range from 1 to 20 parts by weight, based on the total amount of the adhesive. When the content of the medicine is less than 0.01 parts by weight, the pharmaceutical effect of the therapeutic medicine can not be expected sufficiently and the continuous exhibition of the pharmaceutical effect can not be desired in some cases. When the content exceeds 50 parts by weight, the adhesiveness to skin of the base layer will tend to decrease and thus it is not preferable.

The adhesive used in the formulation for percutaneous administration for treating disturbance in micturition of the present invention, contains a low-molecular weight polyisobutylene and a high-molecular weight polyisobutylene and an oil as main bases. The formulation for percutaneous administration for treating disturbance in micturition of the present invention, is excellent in the performances as an adhesive such as coagulation power and adhesion power, by containing the above three kinds of main bases, and thus it can control the drug release efficiently.

The viscosity-average molecular weight of the low-molecular weight polyisobutylene is preferably in the range from 10,000 to 100,000, and the viscosity-average molecular weight of the high-molecular weight polyisobutylene is preferably in the range from 500,000 to 2,500,000.

The oils are preferably selected from the group comprising liquid paraffin having a viscosity of 5 to 100$mm^2/s$, natural and synthetic squalene and squalane.

Squalene or Squalane is a safe hydrocarbon compound and used widely as a cosmetic from the view point of its low irritativeness to skin, and it can be used preferably in the formulation of the present invention.

The contents of the main bases are preferably determined in consideration of the physical characteristics of the formulation as adhesive, such as adhesiveness, coagulation power and drug releasability. Preferably, the content of the low-molecular weight polyisobutylene is in the range from 1 to 60 parts by weight, particularly in the range from 20 to 50 parts by weight, and the content of the high-molecular weight polyisobutylene is in the range from 0.1 to 40 parts by weight, particularly in the range from 10 to 30 parts by weight, based on the total amount of the adhesive. If the content of the low-molecular weight polyisobutylene is less than 1 parts by weight, adhesiveness is poor, and if it exceeds 60 parts by weight, the coagulation power is poor and thus it is not preferable. Further, if the content of the high-molecular weight polyisobutylene is less than 0.1 parts by weight, the coagulation power is poor, and if it exceeds 40 parts by weight, adhesiveness is poor and thus it is not preferable.

The content of the oils is preferably in the range from 10 to 60 parts by weight, more preferably in the range from 20 to 50 parts by weight based on the total amount of the adhesive. By containing the oils, a decrease of the irritativeness to skin and an improvement of the drug releasability may be attained. However, if the content exceeds 60 parts by weight, the coagulation power as a pharmaceutical formulation and the adhesiveness and stability of the formulation, may be avoided in some cases. Further, if the content of the oils is less than 10 parts by weight, the adhesion power is deficient, and the sufficient adhesiveness can not be given, and thus it is not preferable.

The adhesive used in the formulation for percutaneous administration for treating disturbance in micturition of the present invention may further contain styrene-isoprene-styrene block copolymer. By containing the styrene-isoprene-styrene block copolymer, the coagulation power of the adhesive is further improved, and the exudation and the like during storage of the formulation can be prevented.

When the adhesive contains the styrene-isoprene-styrene block copolymer, in consideration of the physical properties as the adhesive of the formulation such as adhesiveness and coagulation power and the drug releasability, based on the total amount of the adhesive, the adhesive preferably contains 1 to 30 parts by weight, particularly 2 to 20 parts by weight of low-molecular weight polyisobutylene, 0.1 to 20 parts by weight, particularly 0.1 to 10 parts by weight of high-molecular weight polyisobutylene, 5 to 50 parts by weight, particularly 10 to 40 parts by weight of the styrene-isoprene-styrene block copolymer. The content of the low-molecular weight polyisobutylene is less than 1 parts by weight, the adhesiveness is poor, and if it exceeds 30 parts by weight, the coagulation power is poor, and thus it is not preferable. In addition, the content of the high-molecular weight polyisobutylene is less than 0.1 parts by weight, the coagulation power is poor, and if it exceeds 20 parts by weight, the adhesiveness is poor, and thus it is not preferable. Further, if the content of the styrene-isoprene-styrene block copolymer is less than 5 parts by weight, the coagulation power is poor, and it exceeds 50 parts by weight, the drug releasability is poor, and thus it is not preferable.

Moreover, the formulation for percutaneous administration for treating disturbance in micturition of the present invention, may contain a transdermal adsorption enhancer, if desired. The transdermal adsorption enhancer which may be used in the present invention is not limited to, but terpene oils such as 1-menthol, peppermint oil and d-limonene, aliphatic acid esters such as glyceryl monolaurate, glyceryl monooleate and diethyl sebacate, azacycloalkanes such as Azon and 1-[2-(decyl thio)ethyl]azacyclopentane-2-one, other oleic acid, lauric acid, myristic acid, oleyl alcohol, 1-[2[(decyl thio)ethyl]azacyclopentane-2-one (hereinafter it is abbreviated as "HPE-101") and the like may be exemplified. One of more of these transdermal absorption enhancers are contained in an amount of 15 parts by weight or less, preferably in the range from 0.5 to 5 weight parts, based on the total amount of the adhesive.

In addition, in the base of the adhesive of the present invention, a tackifying resin, a solubilizer or a solution adjuvant, or a chemically stable filler may be contained, if desired. By adding the tackifying resin and filler, the constant releasability may be attained for a long time period without deteriorating the adhesiveness and coagulation power of the base.

As the tackifying resin which may be used in the present invention, the resin which is in crystalline state and the softening point of which is in the range from 50° to 250° C., is preferable. As the concrete examples, rosin or its derivatives, terpene resin, terpene, phenol resins, petroleum resin, alkyl-phenol resin, xylene resin and the like may be exemplified. One or more of these resins may be preferably contained in an amount 50 parts by weigh or less, particularly in the range from 5 to 40 parts by weight, based on the total amount of the formulation for percutaneous administration for treating disturbance in micturition.

As the solubilizer or solution adjuvant, crotamiton, (poly) ethylene glycol, (poly)propylene glycol and the like may be exemplified. One or more of the solubilizers or solution adjuvants are preferably contained in an amount of 10 parts by weight or less, particularly in the range from 0.1 to 5 parts by weight, based on the total amount of the formulation for percutaneous administration for treating disturbance in micturition.

Further, as the fillers, chemically stable fillers are preferable, and titanium oxide, zinc oxide, talc, silicic anhydride, magnesium silicate, aluminum silicate, polyethylene beads, polystyrene beads, zinc stearate and the like may be exemplified concretely. The particle diameter of the filler is desirably 20 μm or less, particularly in the range from 0.5 to 10 μm. One or more of the fillers may be contained in an amount of 10 parts by weight or less, preferably in the range from 0.1 to 5 parts by weight, based on the total amount of the formulation for percutaneous administration for treating disturbance in micturition.

The formulation for percutaneous administration for treating disturbance in micturition of the present invention, is preferably formed into a base layer by applying the above adhesive onto the surface of a backing.

The backings which may be used in the formulation for percutaneous administration for treating disturbance in micturition of the present invention, are not limited to, but the backings having flexibility to the extent that extreme unconformability is not produced when adhered to skin, are preferable. For example, a single layer film comprising a plastic film such as polyethylene, polypropylene, polyester, polyvinyl acetate, ethylene-vinyl acetate copolymer, polyvinyl chloride and polyurethane, a metal foil such as aluminum foil and tin foil, non-woven fabric, fabric, or paper and the like, and laminated layers having the layers, may be exemplified.

Further, in order to improve the sealability and adhesiveness of these backings to the base layer, coroma discharge treatment, plasma treatment, oxidation treatment and the like are desirably made on the base layer-forming surface of the substrate.

The exposed surface of the base layer of the formulation for percutaneous administration for treating disturbance in micturition of the present invention, is desirably covered and protected with a release liner such as paper, plastics and the like which had been release-treated by applying silicone resin, fluorocarbon polymer and the like, by just before the administration to skin.

The formulation for percutaneous administration for treating disturbance in micturition of the present invention, is appropriately administered percutaneously in an amount of 1 to 50 mg on the basis of the medicine for treating disturbance in micturition, at an interval from once/a day to once/two days, but it can be administered at an interval of one time/three days.

BRIEF DESCRIPTION OF THE DRAWINGS

In FIGS. 1 and 2, ○ shows the results of the formulation of the following Example 1, ● shows the formulation of the following Example 2, □ shows the formulation of the following Example 3, ■ shows the formulation of the following example 4, ◇ shows the formulation of the following Example 5, X shows the formulation of the following Example 6, ◨ shows the formulation of the following Example 7, ◆ shows the formulation of the following Comparative Example 1, Δ shows the formulation of the following Comparative Example 2, ▯ shows the formulation of the following Comparative Example 3, | shows the formulation of the following Comparative Example 4, ▥ shows the formulation of the following Comparative Example 19, and ⊠ shows the formulation of Comparative Example 20.

EXAMPLES

The present invention will be explained in more detail with Examples, hereinafter.

Example 1

| | |
|---|---|
| High-molecular weight Polyisobutylene (viscosity-average molecular weight: 1,110,000) | 15.5 parts by weight |
| Low-molecular weight Polyisobutylene (viscosity-average *molecular weight: 40,000) | 16.5 parts by weight |
| Squalene | 45.0 parts by weight |
| Hydrogenated rosin ester | 10.0 parts by weight |
| Peppermint Oil | 3.0 parts by weight |

To a polyisobutylene solution obtained by dissolving a composition containing the above components in hexane (total solids: 25.0 wt %), oxybutynin was added and mixed so as to have an oxybutynin content of 10 parts by weight when dried. The obtained mixture was applied onto a release liner so as to have a thickness of 50 μm after drying, and dried to form a base layer.

Then, the base layer thus obtained was laminated on a polyester film (thickness: 25 μm) to obtain a formulation for percutaneous administration for treating disturbance in micturition of the present invention.

Example 2

| | |
|---|---|
| High-molecular weight Polyisobutylene (viscosity-average molecular weight: 1,110,000) | 17.0 parts by weight |
| Low-molecular weight Polyisobutylene (viscosity-average molecular weight: 40,000) | 26.0 parts by weight |
| Liquid paraffin (Crystol (Registered Trademark) 352) | 44.0 parts by weight |
| HPE-101 (1-[2-(decylthio)ethyl]azacyclopentane-2-one: generic name:pirotiodecane) | 3.0 parts by weight |

A formulation for percutaneous administration for treating disturbance in micturition of the present invention was obtained in the same manner as described in Example 1 except that the above composition containing the above components was used.

Example 3

| | |
|---|---|
| High-molecular weight Polyisobutylene (viscosity-average molecular weight: 990,000) | 22.0 parts by weight |
| Low-molecular weight Polyisobutylene (viscosity-average molecular weight: 30,000) | 25.0 parts by weight |
| Liquid paraffin (Crystol (Registered Trademark ) 352) | 43.0 parts by weight |

A formulation for percutaneous administration for treating disturbance in micturition of the present invention was obtained in the same manner as described in Example 1, except that the above composition containing the above components was used and that oxybutynin hydrochloride was used in place of oxybutynin.

Example 4

| | |
|---|---|
| High-molecular weight Polyisobutylene (viscosity-average molecular weight: 1,100,000) | 2.0 parts by weight |
| Low-molecular weight Polyisobutylene (viscosity-average molecular weight: 40,000) | 7.0 parts by weight |
| Styrene-isoprene-styrene Block copolymer | 1.0 parts by weight |
| Liquid paraffin (Crystol (Registered Trademark) 352) | 34.0 parts by weight |
| Hydrogenated rosin ester | 27.0 parts by weight |
| HPE-101 (1-[2-(decylthio)ethyl]-azacyclopentane-2-one: generic name: pirotiodecane) | 3.0 parts by weight |
| Antioxidant | 1.0 parts by weight |

Oxybutynin was added to the composition containing the above components so as to have an oxybutynin content of 10 weight parts. The mixture was heated up to 180° C. under nitrogen flow, and mixed and stirred. After stirring for two hours, the obtained mixture was applied on a release liner so as to have a thickness of 50 μm to form a base layer.

Then, the base layer thus obtained was laminated on a polyester film (thickness: 25 μm) to form a formulation for percutaneous administration for treating disturbance in micturition of the present invention.

Example 5

| | |
|---|---|
| High-molecular weight Polyisobutylene (viscosity-average molecular weight: 1,600,000) | 1.5 parts by weight |
| Low-molecular weight Polyisobutylene (viscosity-average molecular weight: 30,000) | 6.5 parts by weight |

-continued

| | |
|---|---|
| Styrene-isoprene-styrene Block copolymer | 13.0 parts by weight |
| Liquid paraffin (Crystol (Registered Trademark) 352) | 30.0 parts by weight |
| Liquid paraffin (Crystol (Registered Trademark) 52) | 7.0 parts by weight |
| Hydrogenated rosin ester | 26.0 parts by weight |
| Antioxidant | 1.0 parts by weight |

A formulation for percutaneous administration for treating disturbance in micturition of the present invention was obtained in the same manner as described in Example 3, except that the above composition containing the above components was used and that oxybutynin was used so as to have a content of 15 parts by weight in place of oxybutynin hydrochloride.

Example 6

| | |
|---|---|
| High-molecular weight Polyisobutylene (viscosity-average molecular weight: 1,110,000) | 2.6 parts by weight |
| Low-molecular weight Polyisobutylene (viscosity-average molecular weight: 40,000) | 10.2 parts by weight |
| Styrene-isoprene-styrene Block copolymer | 20.0 parts by weight |
| Liquid paraffin | 21.0 parts by weight |
| Hydrogenated rosin ester | 35.2 parts by weight |
| Crotamiton | 5.0 parts by weight |
| Antioxidant | 1.0 parts by weight |

A formulation for percutaneous administration for treating disturbance in micturition of the present invention was obtained in the same manner as described in Example 4, except that the above composition containing the above components was used and that oxybutynin was used so as to have a content of 5 parts by weight in place of oxybutynin hydrochloride.

Example 7

| | |
|---|---|
| High-molecular weight Polyisobutylene (viscosity-average molecular weight: 1,600,000) | 2.4 parts by weight |
| Low-molecular weight polyisobutylene (viscosity-average molecular weight: 30,000) | 9.7 parts by weight |
| styrene-isoprene-styrene Block copolymer | 18.1 parts by weight |
| Liquid paraffin | 19.8 parts by weight |
| Hydrogenated rosin ester | 34.0 parts by weight |
| Crotamiton | 5.0 parts by weight |
| Antioxidant | 1.0 parts by weight |

A formulation for percutaneous administration for treating disturbance in micturition of the present invention was obtained in the same manner as described in Example 4, except that the above composition containing the above components was used and that oxybutynin was used so as to have a content of 10 parts by weight in place of oxybutynin hydrochloride.

Example 8

A formulation for percutaneous administration for treating disturbance in micturition of the present invention was obtained in the same manner as described in Example 1, except that vamicamide was used in place of oxybutynin.

Example 9

| | |
|---|---|
| High-molecular weight Polyisobutylene (viscosity-average molecular weight: 900,000) | 1.0 parts by weight |
| Low-molecular weight Polyisobutylene (viscosity-average molecular weight: 55,000) | 16.0 parts by weight |
| Styrene-isoprene-styrene Block copolymer | 20.0 parts by weight |
| Squalene | 26.0 parts by weight |
| Hydrogenated rosin ester | 6.0 parts by weight |
| Antioxidant | 1.0 parts by weight |

A formulation for percutaneous administration for treating disturbance in micturition of the present invention was obtained in the same manner as described in Example 3, except that the above composition containing the above components was used and that vamicamide was used so as to have a content of 30 parts by weight in place of oxybutynin hydrochloride.

Example 10

A formulation for percutaneous administration for treating disturbance in micturition of the present invention was obtained in the same manner as described in Example 1, except that naftopidil was used in place of oxybutynin.

Example 11

| | |
|---|---|
| High-molecular weight Polyisobutylene (viscosity-average molecular weight: 1,900,000) | 2.0 parts by weight |
| Low-molecular weight Polyisobutylene (viscosity-average molecular weight: 40,000) | 10.0 parts by weight |
| Styrene-isoprene-styrene Block copolymer | 8.0 parts by weight |
| Liquid paraffin (Crystol (Registered Trademark) 352) | 28.0 parts by weight |
| Hydrogenated rosin ester | 18.0 parts by weight |
| Antioxidant | 1.0 parts by weight |

A formulation for percutaneous administration for treating disturbance in micturition of the present invention was obtained in the same manner as described in Example 3, except that the above composition containing the above components was used and that naftopidil was used so as to have a content of 35 parts by weight in place of oxybutynin hydrochloride.

Example 12

A formulation for percutaneous administration for treating disturbance in micturition of the present invention was obtained in the same manner as described in Example 2, except that prazosin was used in place of oxybutynin.

Example 13

| | |
|---|---|
| High-molecular weight Polyisobutylene (viscosity-average molecular weight: 900,000) | 1.0 parts by weight |
| Low-molecular weight Polyisobutylene (viscosity-average molecular weight: 15,000) | 22.0 parts by weight |
| Styrene-Isoprene-styrene Block copolymer | 13.0 parts by weight |
| Liquid paraffin (Crystol (Registered Trademark) 352) | 15.0 parts by weight |
| Hydrogenated rosin ester | 15.0 parts by weight |
| HPE-101 (1-[2-(decylthio)ethyl] azacyclopentane-2-one: generic name: pirotiodecane) | 3.0 parts by weight |
| Antioxidant | 1.0 parts by weight |

A formulation for percutaneous administration for treating disturbance in micturition of the present invention was obtained in the same manner as described in Example 3, except that the above composition containing the above components was used and that prazosin was used so as to have a content of 30 parts by weight in place of oxybutynin hydrochloride.

Example 14

A formulation for percutaneous administration for treating disturbance in micturition of the present invention was obtained in the same manner as described in Example 3, except that bunazocin was used in place of oxybutynin hydrochloride.

Example 15

| | |
|---|---|
| High-molecular weight Polyisobutylene (viscosity-average molecular weight: 600,000) | 34.0 parts by weight |
| Low-molecular weight Polyisobutylene (viscosity-average molecular weight: 80,000) | 15.0 parts by weight |
| Liquid paraffin (Crystol (Registered Trademark) 352) | 18.0 parts by weight |
| Peppermint oil | 3.0 parts by weight |

A formulation for percutaneous administration for treating disturbance in micturition of the present invention was obtained in the same manner as described in Example 1, except that the above composition containing the above components was used and that bunazocin was used so as to have a content of 35 parts by weight in place of oxybutynin.

Example 16

A formulation for percutaneous administration for treating disturbance in micturition of the present invention was obtained in the same manner as described in Example 4, except that terazosin was used in place of oxybutynin.

Example 17

| | |
|---|---|
| High-molecular weight Polyisobutylene (viscosity-average molecular weight: 1,110,000) | 12.0 parts by weight |
| Low-molecular weight Polyisobutylene (viscosity-average molecular weight: 80,000) | 50.0 parts by weight |
| Liquid paraffin (Crystol (Registered Trademark) 352) | 7.0 parts by weight |
| Hydrogenated rosin ester | 8.0 parts by weight |
| Peppermint oil | 3.0 parts by weight |

A formulation for percutaneous administration for treating disturbance in micturition of the present invention was obtained in the same manner as described in Example 1, except that the above composition containing the above components was used and that terazosin was used so as to have a content of 20 parts by weight in place of oxybutynin.

Example 18

A formulation for percutaneous administration for treating disturbance in micturition of the present invention was obtained in the same manner as described in Example 4, except that terodiline hydrochloride was used in place of oxybutynin.

Example 19

| | |
|---|---|
| High-molecular weight Polyisobutylene (viscosity-average molecular weight: 1,900,000) | 12.0 parts by weight |
| Low-molecular weight Polyisobutylene (viscosity-average molecular weight: 15,000) | 20.0 parts by weight |
| Liquid paraffin (Crystol (Registered Trademark) 352) | 20.0 parts by weight |
| Peppermint Oil | 3.0 parts by weight |

A formulation for percutaneous administration for treating disturbance in micturition of the present invention was obtained in the same manner as described in Example 1, except that the above composition containing the above components was used and that terodiline hydrochloride was used so as to have a content of 45 parts by weight in place of oxybutynin.

Example 20

A formulation for percutaneous administration for treating disturbance in micturition of the present invention was obtained in the same manner as described in Example 4, except that inaperisone was used in place of oxybutynin.

Example 21

| | |
|---|---|
| High-molecular weight Polyisobutylene (viscosity-average molecular weight: 900,000) | 1.0 parts by weight |
| Low-molecular weight Polyisobutylene (viscosity-average molecular weight: 40,000) | 8.0 parts by weight |
| Styrene-isoprene-styrene Block copolymer | 40.0 parts by weight |
| Liquid paraffin (Crystol (Registered Trademark) 352) | 10.0 parts by weight |
| Hydrogenated rosin ester | 10.0 parts by weight |
| HPE-101 (1[2-(decylthio)ethyl]-azacyclopentane-2-one: generic name: pirotiodecane) | 5.0 parts by weight |
| Antioxidant | 1.0 parts by weight |

A formulation for percutaneous administration for treating disturbance in micturition of the present invention was obtained in the same manner as described in Example 3, except that the above composition containing the above components was used and that inaperisone was used so as to have a content of 25 parts by weight in place of oxybutynin hydrochloride.

Example 22

A formulation for percutaneous administration for treating disturbance in micturition of the present invention was obtained in the same manner as described in Example 5, except that propiverine was used in place of oxybutynin.

Example 23

| | |
|---|---|
| High-molecular weight Polyisobutylene (viscosity-average molecular weight: 600,000) | 15.0 parts by weight |
| Low-molecular weight Polyisobutylene (viscosity-average molecular weight: 40,000) | 12.0 parts by weight |
| Styrene-isoprene-styrene Block copolymer | 20.0 parts by weight |
| Liquid paraffin (Crystol (Registered Trademark) 352) | 22.0 parts by weight |
| Antioxidant | 1.0 parts by weight |

A formulation for percutaneous administration for treating disturbance in micturition of the present invention was obtained in the same manner as described in Example 3, except that the above composition containing the above components was used and that propiverine was used so as to have a content of 30 parts by weight in place of oxybutynin hydrochloride.

Example 24

A formulation for percutaneous administration for treating disturbance in micturition of the present invention was obtained in the same manner as described in Example 5, except that tamsulosin was used in place of oxybutynin.

Example 25

| | |
|---|---|
| High-molecular weight Polyisobutylene (viscosity-average molecular weight: 1,110,000) | 2.0 parts by weight |
| Low-molecular weight Polyisobutylene (viscosity-average molecular weight: 90,000) | 8.0 parts by weight |
| Styrene-isoprene-styrene Block copolymer | 19.0 parts by weight |
| Liquid paraffin (Crystol (Registered Trademark)352) | 24.0 parts by weight |
| Hydrogenated rosin ester | 21.0 parts by weight |
| Antioxidant | 1.0 parts by weight |

A formulation for percutaneous administration for treating disturbance in micturition of the present invention was obtained in the same manner as described in Example 3, except that the above composition containing the above components was used and that tamsulosin was used so as to have a content of 25 parts by weight in place of oxybutynin hydrochloride.

Example 26

| | |
|---|---|
| High-molecular weight Polyisobutylene (viscosity-average molecular weight: 2,200,000) | 1.0 parts by weight |
| Low-molecular weight Polyisobutylene (viscosity-average molecular weight: 30,000) | 7.0 parts by weight |
| Styrene-isoprene-styrene Block copolymer | 18.0 parts by weight |
| Liquid paraffin (Crystol (Registered Trademark) 352) | 39.0 parts by weight |
| Hydrogenated rosin ester | 30.0 parts by weight |
| Antioxidant | 1.9 parts by weight |
| d-Limonene | 3.0 parts by weight |

Oxybutynin was added to the composition containing the above components so as to have a content of oxybutynin of 0.1 weight part. The mixture was heated up to 180° C. under nitrogen gas flow, and mixed and stirred. After stirring for two hours, the obtained mixture was applied onto a release liner so as to have a thickness of 50 μm to form a base layer. Then the base layer thus obtained was laminated on a polyester film (thickness: 25 μm) to obtain a formulation for percutaneous administration, for treating disturbance in micturition.

Example 27

| | |
|---|---|
| High-molecular weight Polyisobutylene (viscosity-average molecular weight: 2,300,000) | 0.5 parts by weight |
| Low-molecular weight Polyisobutylene (viscosity-average molecular weight: 50,000) | 9.0 parts by weight |
| Styrene-isoprene-styrene Block copolymer | 21.0 parts by weight |
| Liquid paraffin (Crystol (Registered Trademark) 352) | 36.0 parts by weight |
| Hydrogenated rosin ester | 27.0 parts by weight |
| Antioxidant | 1.5 parts by weight |

Oxybutynin was added to the composition containing the above components so as to have a content of oxybutynin of 5 weight part. The mixture was heated up to 180° C. under nitrogen gas flow, and mixed and stirred. After stirring for two hours, the obtained mixture was applied onto a release liner so as to have a thickness of 50 μm to form a base layer. Then the base layer thus obtained was laminated on a polyester film (thickness: 25 μm) to obtain a formulation for percutaneous administration for treating disturbance in micturition.

Example 28

| | |
|---|---|
| High-molecular weight Polyisobutylene (viscosity-average molecular weight: 1,900,000) | 0.3 parts by weight |
| Low-molecular weight Polyisobutylene (viscosity-average molecular weight: 90,000) | 12.7 parts by weight |
| Styrene-isoprene-styrene Block copolymer | 24.0 parts by weight |
| Liquid paraffin (Crystol (Registered Trademark) 352) | 28.0 parts by weight |
| Hydrogenated rosin ester | 30.0 parts by weight |
| Antioxidant | 2.0 parts by weight |

Oxybutynin was added to the composition containing the above components so as to have a content of oxybutynin of 3 weight part. The mixture was heated up to 180° C. under nitrogen gas flow, and mixed and stirred. After stirring for two hours, the obtained mixture was applied onto a release liner so as to have a thickness of 50 μm to form a base layer. Then the base layer thus obtained was laminated on a polyester film (thickness: 25 μm) to obtain a formulation for percutaneous administration for treating disturbance in micturition.

Comparative Example 1

| | |
|---|---|
| Styrene-isoprene-styrene Block copolymer | 18.0 parts by weight |
| Liquid paraffin (Crystol (Registered Trademark) 352) | 34.0 parts by weight |
| Hydrogenated rosin ester | 34.0 parts by weight |
| HPE - 101(1-[2-(decylthio)ethyl]azacyclopentane-2-one: generic name: pirotiodecane) | 3.0 parts by weight |
| Antioxidant | 1.0 parts by weight |

A formulation for percutaneous administration for treating disturbance in micturition in the same manner as described in Example 4, except that the composition containing the above components.

Comparative Example 2

| | |
|---|---|
| Gelatin | 15.0 parts by weight |
| Nikasol TS - 620 | 5.0 parts by weight |
| (88% partial saponified) Polyvinyl alcohol | 10.0 parts by weight |
| Glycerin | 25.6 parts by weight |
| p-Oxy methyl benzoate | 0.2 parts by weight |
| Aluminum glycinate | 0.2 parts by weight |
| Purified water | 40.0 parts by weight |
| Oxybutynin | 4.0 parts by weight |

In the purified water heated to 70° C., the above gelatin, polyvinyl alcohol and Nikasol TS-620 were dissolved sequently to obtain a solution (I). Then, after dissolving p-oxy methyl benzoate and oxybutynin in glycerin heated to 70° C., a dispersion, in which maleic anhydride-methyl vinyl ether block copolymer and aluminum glycinate were dispersed homogeneously, was added to the above solution (I) and mixed. Then the mixture thus obtained was applied on a release liner treated with silicone to have a thickness of 300 μm, and it was laminated on the PET-treated surface of unwoven fabric, in which one surface had been treated with PET, to obtain a cataplasm containing oxybutynin.

Comparative Example 3

| | |
|---|---|
| 2-Ethylhexyl acrylate | 75.0 parts by weight |
| Methyl methacrylate | 15.0 parts by weight |
| Acrylic acid | 10.0 parts by weight |
| Azobisisobutyronitrile | 0.02 parts by weight |

The composition containing the above components was polymerized at 60° C. for 48 hours in ethyl acetate/toluene (1/1) solvent so as to have total solids of 40 weight %. To the obtained polymer solution, 0.1 parts by weight of isocyanate crosslinking agent and oxybutynin were added so as to have a content of oxybutynin of 10 wt % when dried, and applied onto a liner treated with silicone to have a thickness of 50 μm, and dried. Then the base layer thus obtained was laminated on a polyester film (thickness: 25 μm) to obtain an acrylic tape containing oxybutynin.

Comparative Example 4

| | |
|---|---|
| Gelatin | 3.0 parts by weight |
| Maleic anhydride - methyl vinyl ether copolymer (GANTREZ 169) | 3.0 parts by weight |
| Partial saponified polyvinyl alcohol | 5.0 parts by weight |
| Sodium polyacrylate | 2.0 parts by weight |
| Glycerin | 31.0 parts by weight |
| p-Oxy methyl benzoate | 0.2 parts by weight |
| Purified water | 49.6 parts by weight |
| Oxybutynin | 4.0 parts by weight |

In the purified water heated to 70° C., the above gelatin, sodium polyacrylate, maleic anhydride-methyl vinyl ether copolymer were dissolved sequently to obtain a solution (I). Then, after dissolving partial saponified polyvinyl alcohol, p-oxy methyl benzoate and oxybutynin in glycerin heated to 70° C., it was added to the above solution (I) and mixed. The mixture was applied on a release liner treated with silicone to have a thickness of 300 μm. Then it was laminated on the PET-treated surface of unwoven fabric, in which one surface had been treated with PET, to obtain a cataplasm containing oxybutynin.

Comparative Example 5

A formulation for percutaneous administration for treating disturbance in micturition was obtained in the same manner as described in Example 1 except that 32.0 parts by weight of high-molecular weight polyisobutylene (viscosity-average molecular weight: 1,110,000) was used and that low-molecular weight polyisobutylene was not used.

Comparative Example 6

A formulation for percutaneous administration for treating disturbance in micturition was obtained in the same manner as described in Example 1 except that 32.0 parts by weight of low-molecular weight polyisobutylene (viscosity-average molecular weight: 40,000) was used and that high-molecular weight polyisobutylene was not used.

Comparative Example 7

A formulation for percutaneous administration for treating disturbance in micturition was obtained in the same manner as described in Example 2 except that 43.0 parts by weight of high-molecular weight polyisobutylene (viscosity-average molecular weight: 1,110,000) was used and that low-molecular weight polyisobutylene was not used.

Comparative Example 8

A formulation for percutaneous administration for treating disturbance in micturition was obtained in the same manner as described in Example 2 except that 43.0 parts by weight of low-molecular weight polyisobutylene (viscosity-average molecular weight: 40,000) was used and that high-molecular weight polyisobutylene was not used.

Comparative Example 9

A formulation for percutaneous administration for treating disturbance in micturition was obtained in the same manner as described in Example 3 except that 47.0 parts by weight of high-molecular weight polyisobutylene (viscosity-average molecular weight: 990,000) was used and that low-molecular weight polyisobutylene was not used.

Comparative Example 10

A formulation for percutaneous administration for treating disturbance in micturition was obtained in the same manner as described in Example 3 except that 47.0 parts by weight of low-molecular weight polyisobutylene (viscosity-average molecular weight: 30,000) was used and that high-molecular weight polyisobutylene was not used.

Comparative Example 11

A formulation for percutaneous administration for treating disturbance in micturition was obtained in the same manner as described in Example 4 except that 9.0 parts by weight of high-molecular weight polyisobutylene (viscosity-average molecular weight: 1,110,000) was used and that low-molecular weight polyisobutylene was not used.

Comparative Example 12

A formulation for percutaneous administration for treating disturbance in micturition was obtained in the same manner as described in Example 4 except that 9.0 parts by weight of low-molecular weight polyisobutylene (viscosity-average molecular weight: 40,000) was used and that high-molecular weight polyisobutylene was not used.

Comparative Example 13

A formulation for percutaneous administration for treating disturbance in micturition was obtained in the same manner as described in Example 5 except that 8.0 parts by weight of high-molecular weight polyisobutylene (viscosity-average molecular weight: 1,600,000) was used and that low-molecular weight polyisobutylene was not used.

Comparative Example 14

A formulation for percutaneous administration for treating disturbance in micturition was obtained in the same manner as described in Example 5 except that 8.0 parts by weight of low-molecular weight polyisobutylene (viscosity-average molecular weight: 30,000) was used and that high-molecular weight polyisobutylene was not used.

Comparative Example 15

A formulation for percutaneous administration for treating disturbance in micturition was obtained in the same manner as described in Example 6 except that 12.8 parts by weight of high-molecular weight polyisobutylene (viscosity-average molecular weight: 1,110,000) was used and that low-molecular weight polyisobutylene was not used.

Comparative Example 16

A formulation for percutaneous administration for treating disturbance in micturition was obtained in the same manner as described in Example 6 except that 12.8 parts by weight of low-molecular weight polyisobutylene (viscosity-average molecular weight: 40,000) was used and that high-molecular weight polyisobutylene was not used.

Comparative Example 17

A formulation for percutaneous administration for treating disturbance in micturition was obtained in the same manner as described in Example 7 except that 12.1 parts by weight of high-molecular weight polyisobutylene (viscosity-average molecular weight: 1,600,000) was used and that low-molecular weight polyisobutylene was not used.

Comparative Example 18

A formulation for percutaneous administration for treating disturbance in micturition was obtained in the same manner as described in Example 7 except that 12.1 parts by weight of low-molecular weight polyisobutylene (viscosity-average molecular weight: 30,000) was used and that high-molecular weight polyisobutylene was not used.

Comparative Example 19
(A Manufacture of formulation for percutaneous administration for treating disturbance in micturition using the same composition and the same method as described in Example 3 of the Japanese Un-Examined Patent Publication No.Hei 4-273818)

| Ethylhexyl acrylate (manufactured by Rohmfahm, Germany) | 82.0 parts by weight |
| Propylene glycol | 8.0 parts by weight |
| Oxybutynin | 10.0 parts by weight |

A suspension of ethylhexyl acrylate (7927/80, manufactured by Rohmfahm) was heated at 120° C. for 30 min. to obtain an adhesive layer. After cooling, oxybutynin dissolved in propylene glycol was mixed with it, to have an adhesive for percutaneous absorption. The adhesive was applied on the surface of paper treated with polyethylene, being a release liner, so as to have a thickness of 50 $\mu$m, to obtain a drug-containing layer of a patch containing oxybutynin. Then, the drug-containing layer was laminated on the treated surface of a porous polyethylene film, being a backing, (pore diameter: approx.0.2 mm, distance between pores: 1.5 mm) in which the surface had been oxidation-treated, so that the opposite surface of the linear liner was contacted, to obtain a formulation for percutaneous administration for treating disturbance in micturition containing oxybutynin.

Comparative Example 20
(A Manufacture of formulation for percutaneous administration for treating disturbance in micturition using the same composition and the same method as described in Example 3 of the Japanese Un-Examined Patent Publication No.Hei 4-99719)

| Purified Water | 31.5 parts by weight |
| Oleic acid | 1.0 parts by weight |
| Glycerin | 15.0 parts by weight |
| Butanediol | 15.0 parts by weight |
| Sodium carboxymethylcellulose | 9.0 parts by weight |
| Sodium polyacrylate | 7.0 parts by weight |
| Gelatin | 4.0 parts by weight |
| Kaolin | 7.0 parts by weight |
| Citric acid | 0.5 parts by weight |
| Oxybutynin hydrochloride | 10.0 parts by weight |

Oxybutynin hydrochloride was dissolved in water and it was mixed with the above other components homogeneously to obtain a formulation for percutaneous administration for treating disturbance in micturition containing oxybutynin.

Test Example 1
(Test of stability against change with time)

In order to examine the stabilities against change with time of the formulations obtained in Examples 1 to 7 and Comparative Examples 1 to 18, a test of the remaining amounts of the medicines (Examples 1 to 7 and Comparative Examples 1 to 4) during storage, and of the changes with time of the physical characteristics of the formulations (Examples 1 to 7 and Comparative Examples 1 to 18) were made. The storage condition of each formulation was to seal it in an aluminum package at 40° C. The remaining amount of oxybutynin in each formulation was determined with HPLC method.

In addition, as the physical characteristics, observations on the adhesiveness and appearance were carried out. The adhesiveness was determined by observing the changes with time of the adhesive property (probe tack value (g/cm$^2$) using a probe tack tester (manufactured by Rigaku Kogyo kk). The appearance was evaluated in accordance with the following standards. The results are shown in the Tables 1 and 2.

TABLE 1

Changes with time of remaining amount of Oxybutynin (wt %)

| | Example No. | | | | | | | Comp. Example No. | | | |
|---|---|---|---|---|---|---|---|---|---|---|---|
| | 1 | 2 | 3 | 4 | 5 | 6 | 7 | 1 | 2 | 3 | 4 |
| 1 months | 99.9 | 99.9 | 99.7 | 99.8 | 99.9 | 99.9 | 99.8 | 99.5 | 98.4 | 99.5 | 99.0 |
| 2 months | 99.7 | 99.1 | 99.5 | 99.8 | 99.2 | 99.7 | 99.5 | 99.1 | 96.3 | 97.5 | 85.6 |
| 3 months | 99.1 | 98.3 | 99.1 | 99.8 | 98.5 | 99.3 | 99.2 | 98.9 | 91.0 | 93.5 | 78.6 |
| 6 months | 98.6 | 98.4 | 98.9 | 99.5 | 97.9 | 98.7 | 98.4 | 98.6 | 84.1 | 88.6 | 68.3 |

TABLE 2

Changes with time of physical characteristics of formulations

| | \| Example No. | | | | | | |
|---|---|---|---|---|---|---|---|
| | 1 | 2 | 3 | 4 | 5 | 6 | 7 |
| Initial | | | | | | | |
| Prove tack | 211 | 209 | 211 | 212 | 237 | 310 | 305 |
| Appearance | ⊚ | ⊚ | ⊚ | ⊚ | ⊚ | ⊚ | ⊚ |
| 1 month | | | | | | | |
| Prove tack | 200 | 207 | 210 | 222 | 226 | 308 | 303 |
| Appearance | ⊚ | ⊚ | ⊚ | ⊚ | ⊚ | ⊚ | ⊚ |
| 2 months | | | | | | | |
| Prove tack | 205 | 195 | 208 | 220 | 226 | 307 | 301 |
| Appearance | ⊚ | ⊚ | ⊚ | ⊚ | ⊚ | ⊚ | ⊚ |
| 3 months | | | | | | | |
| Prove tack | 198 | 203 | 205 | 219 | 220 | 305 | 301 |
| Appearance | ⊚ | ⊚ | ⊚ | ⊚ | ⊚ | ⊚ | ⊚ |
| 6 months | | | | | | | |
| Prove tack | 208 | 195 | 204 | 215 | 210 | 301 | 298 |
| Appearance | ⊚ | ⊚ | ⊚ | ⊚ | ⊚ | ⊚ | ⊚ |

| | Comparative Example No. | | | | | | | | |
|---|---|---|---|---|---|---|---|---|---|
| | 1 | 2 | 3 | 4 | 5 | 6 | 7 | 8 | 9 |
| Initial | | | | | | | | | |
| Prove tack | 450 | 50 | 305 | 34 | 99 | 230 | 101 | 242 | 98 |
| Appearance | ⊚ | ⊚ | ⊚ | ⊚ | ⊚ | ⊚ | ⊚ | ⊚ | ⊚ |
| 1 month | | | | | | | | | |
| Prove tack | 420 | 49 | 303 | 32 | 98 | 232 | 98 | 240 | 96 |
| Appearance | ⊚ | ○ | ⊚ | ○ | ⊚ | X | ⊚ | X | ⊚ |
| 2 months | | | | | | | | | |
| Prove tack | 400 | 40 | 306 | 30 | 95 | 240 | 101 | 236 | 97 |
| Appearance | ⊚ | Δ | ⊚ | Δ | ⊚ | X | ⊚ | X | ⊚ |
| 3 months | | | | | | | | | |
| Prove tack | 400 | 32 | 301 | 29 | 97 | 242 | 97 | 243 | 91 |
| Appearance | ⊚ | Δ | ○ | Δ | ⊚ | X | ⊚ | X | ⊚ |
| 6 months | | | | | | | | | |
| Prove tack | 398 | — | 300 | 25 | 95 | 245 | 98 | 241 | 93 |
| Appearance | ⊚ | X | Δ | X | ⊚ | X | ⊚ | X | ⊚ |

| | Comparative Example No. | | | | | | | | |
|---|---|---|---|---|---|---|---|---|---|
| | 10 | 11 | 12 | 13 | 14 | 15 | 16 | 17 | 18 |
| Initial | | | | | | | | | |
| Prove tack | 235 | 108 | 245 | 110 | 252 | 152 | 358 | 161 | 382 |
| Appearance | ⊚ | ⊚ | ⊚ | ⊚ | ⊚ | ⊚ | ⊚ | ⊚ | ⊚ |
| 1 month | | | | | | | | | |
| Prove tack | 248 | 105 | 246 | 105 | 251 | 154 | 352 | 160 | 386 |
| Appearance | X | ⊚ | X | ⊚ | X | ⊚ | X | ⊚ | X |
| 2 months | | | | | | | | | |
| Prove tack | 240 | 102 | 250 | 105 | 248 | 150 | 351 | 158 | 390 |
| Appearance | X | ⊚ | X | ⊚ | X | ⊚ | X | ⊚ | X |
| 3 months | | | | | | | | | |
| Prove tack | 245 | 108 | 252 | 107 | 250 | 155 | 360 | 157 | 395 |
| Appearance | X | ⊚ | X | ⊚ | X | ⊚ | X | ⊚ | X |
| 6 months | | | | | | | | | |
| Prove tack | 242 | 103 | 260 | 108 | 251 | 152 | 355 | 155 | 397 |
| Appearance | X | ⊚ | X | ⊚ | X | ⊚ | X | ⊚ | X |

Probe tack value: (g/cm$^2$)
⊚: unchanged
○: some decrease in viscosity
Δ: some exudation
X: exudation and stringing As it is apparent from the results shown in Table 1, the remaining amounts of oxybutynin in formulations for percutaneous administration for treating disturbance in micturition of the present invention, were scarcely changed and were stable, while the remaining amounts of oxybutynin in the formulations of Comparative Examples were extremely decreased with time and the stability was poor, except Comparative Example 1.

In addition, as it is apparent from the results shown in Table 2, all of the formulations for percutaneous administration for treating disturbance in micturition of Examples of the present invention, exhibited sufficient physical stabilities, while in the formulations of Comparative Examples, the physical stabilities were extremely poor and thus it was proved that the commercialization of the formulations of Comparative Examples was impossible.

Moreover, each formulation for percutaneous administration for treating disturbance in micturition obtained in Examples 8 to 28, showed the same stabilities with time as each formulation for percutaneous administration for treating disturbance in micturition of Examples 1 to 7.

Test Example 2

(Test of irritativenss to skin)

In order to examine the irritativeness to skin of each formulation obtained in Examples 1 to 7 and Comparative Examples 1 to 4, patch test (applied for 48 hours) was carried out on healthy men. The results were shown in the following Table 3.

TABLE 3

| | Examples | | | | | | | Comp. Example | | | |
|---|---|---|---|---|---|---|---|---|---|---|---|
| | 1 | 2 | 3 | 4 | 5 | 6 | 7 | 1 | 2 | 3 | 4 |
| SI value | 10.3 | 7.8 | 9.4 | 13.0 | 14.6 | 7.8 | 9.2 | 24.8 | 30.5 | 45.4 | 21.3 |

Results of the test of irritativenss to skin

SI value: skin irritation index

From the results shown in Table 3, the formulation for percutaneous administration for treating urinary incontinence of the present invention obtained in Examples 1 to 7, were low irritative, while the formulations of Comparative Examples 1 to 4 were high irritative and thus it was apparent that the performances as formulations for percutaneous administration were inferior.

Test Example 3
(Test of transdermal absorption using rats)

Figure 1:
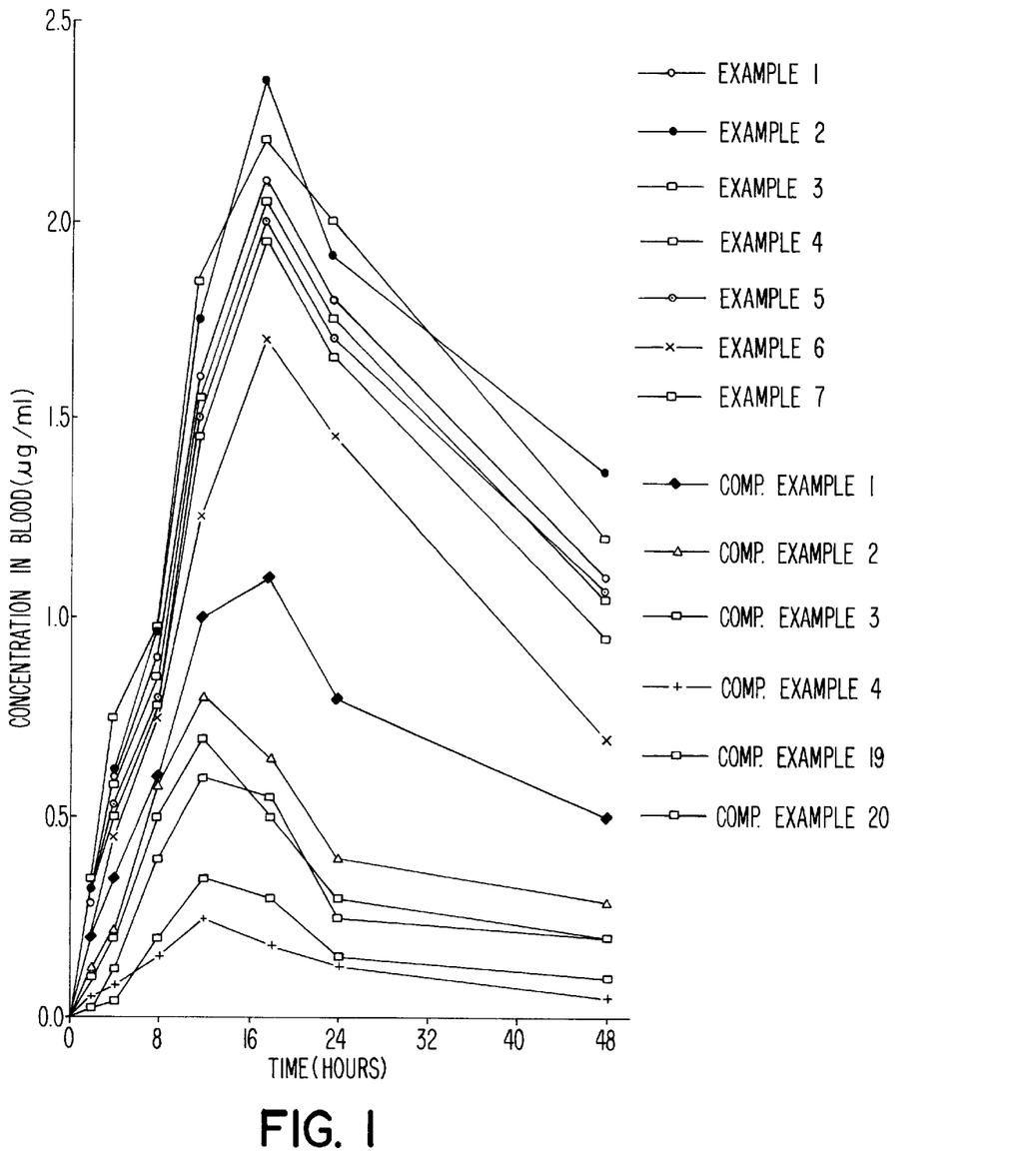
FIG. 1 shows the results of the transdermal absorption test using rats.

The in vivo transdermal absorbability of each formulation obtained in Examples 1 to 7 and Comparative Examples 1 to 4, 19 and 20 was examined using rats. Each formulation formed into a circular shape having a diameter of 2 cm, was applied onto abdomen of depilated rat, and the change with time of blood concentration was determined with gas chromatography. The results were shown in FIG. 1. From the results shown in FIG. 1, the formulations for percutaneous administration for treating disturbance in micturition of the present invention obtained in Examples 1 to 7, apparently had excellent transdermal absorbabilities compared with each formulation of Comparative Examples 1 to 4, 19 and 20.

Test Example 4
(Test of transdermal absorption using human skin)

An investigation on in vitro transdermal absorbability of each formulation obtained in Examples 1 to 7 and Comparative Examples 1 to, 4, 19 and 20 using cadaver skin, was made.

Figure 2:
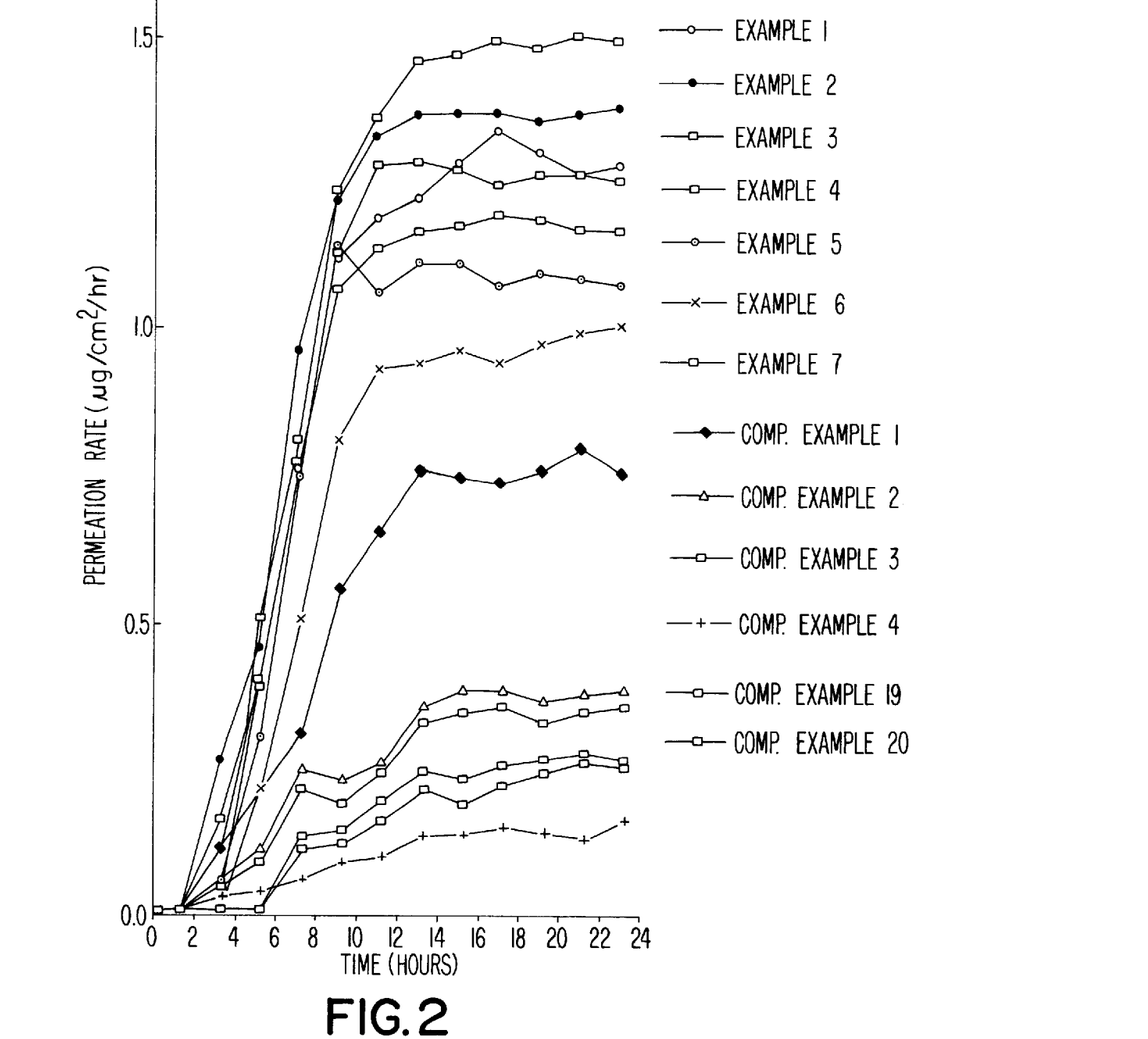
FIG. 2 shows the results of the transdermal absorption test using human skin.

Each formulation formed into a circular shape having a diameter of 3 cm, was applied onto cadaver skin, and then it was set to a flow cell connected to a fraction connecter to determine the drug permeation amounts with time using gas chromatography. The results are shown in FIG. 2. From the results shown in FIG. 2, it was apparent that the formulations for percutaneous administration for treating disturbance in micturition of the present invention obtained in Examples 1 to 7 had more excellent transdermal absorbabilities compared with the formulations of Comparative Examples 1 to 4, 19 and 20.

Test Example 5
(Evaluation test of pharmaceutical effects with cystometry using rats)

The abdominal part of a rat was incised medianly under urethane anesthesia, a catheter having two cavities was inserted into the cupular part of the bladder. The one catheter was connected to a transducer for the measurement of internal pressure of the bladder, and the other catheter was connected to a pump for continuous injection. When saline warmed to 37° C. was injected into the bladder at a rate of 46 $\mu$l/min, a temporary micturition contraction accompanied with micturition was observed after few minutes. At that time, the volume of saline injected until micturition was occurred was regarded as the threshold volume of micturition (VT), the internal pressure of the bladder just before the micturition was regarded as the threshold pressure of micturition (PT), and the maximum internal, pressure at the time of the micturition contraction was regarded as the maximum pressure of micturition ($P_{max}$). The pharmacological actions of the formulations for percutaneous administration for treating disturbance in micturition of the present invention in relation to the three parameters were examined.

The tests were carried out, by applying 2cm$^2$ of the formulation for percutaneous administration for treating disturbance in micturition of the present invention obtained in the above Example 4 to the chest of a rat. The results were shown in FIG. 3.

Figure 3A:
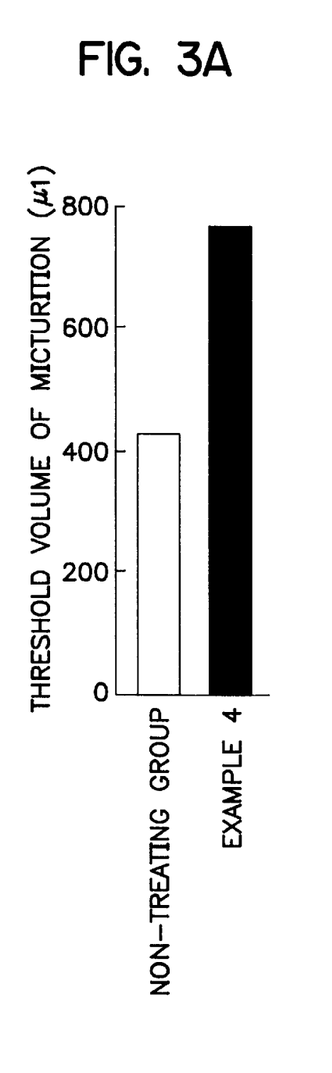
FIG. 3 shows the results of the evaluation test on the pharmaceutical effects with the cystometry using rats.
Figure 3B:
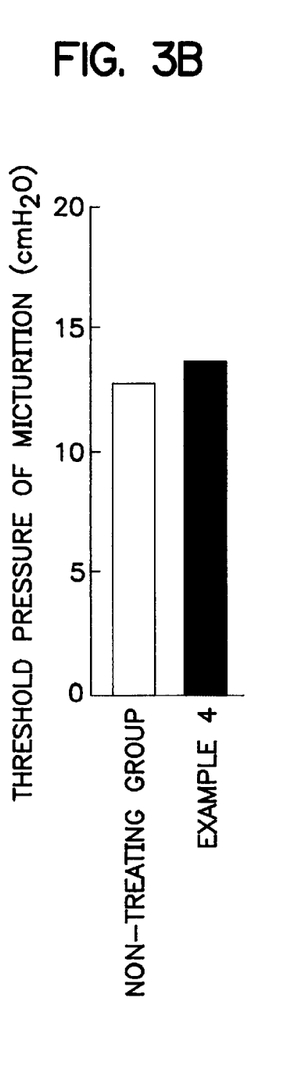
Figure 3C:
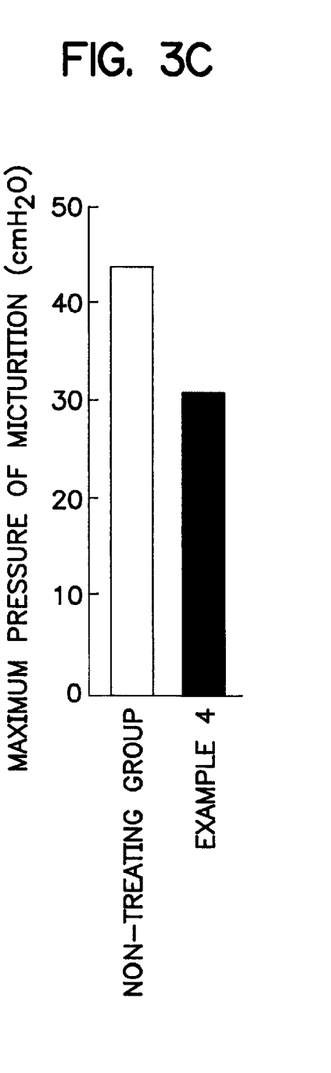

As shown in FIG. 3, in the formulation for percutaneous administration of the present invention, the threshold volume of micturition (VT) increased significantly even after 24 hours from the application, compared with the nontreated group. The larger the threshold volume of micturition (VT), the larger the accumulated amount of urine and the longer the interval of micturition. It can be considered that the increase of the threshold volume of micturition (VT) by applying the formulation for percutaneous administration of the present invention, was due to the synergistic effect of the relaxing action on bladder smooth muscle and the anticholinergic action of oxybutynin which is the medicine for treating disturbance in micturition contained in the formulation.

In addition, the change of the threshold pressure of micturition (PT) was not observed compared with the non-treated group, but the maximum pressure of micturition ($P_{max}$) decreased significantly. It can be supposed that the significant decrease of the maximum pressure of micturition ($P_{max}$) was due to the anticholinergic action of oxybutynin which is a medicine for treating disturbance in micturition contained in the formulation of the present invention.

From the results of the above test, it was proved that the formulation for percutaneous administration for treating disturbance in micturition of the present invention, showed excellent and continuing pharmaceutical effects.

Industrial Applicability

The formulation for percutaneous administration for treating disturbance in micturition of the present invention is excellent in stability against change with time, low irritative to skin, and excellent in transdermal absorbability, by using the above base components. Further, since the contained medicine for treating disturbance in micturition is released continuously directly in the circulating blood via skin, the medicine is not metabolized due to the fast-pass effect occurred in liver at the time of oral administration, and the side-effects due to the temporary increase in the concentrations in blood are not occurred. In addition, the bioavailability of the medicine for treating disturbance in micturition is increased, and the medicine can be administered in the bodies efficiently.

Further, by containing a transdermal absorption enhancer if desired, a more sufficient transdermal absorbability may be attained, and an excellent effect may be exhibited.

Moreover, since the number of times of administration (a number of times of administration per unit hours) may be small using the formulation for percutaneous administration for treating disturbance in micturition of the present invention, the damages given to skin may be controlled at a minimum.

We claim:

1. A formulation without scopolamine for percutaneous administration for treating disturbance in micturition, which comprises a medicine for treating disturbance in micturition in an adhesive, said adhesive containing a low-molecular weight polyisobutylene having a viscosity-average molecular weight of from about 10,000 to 100,000, a high-molecular weight polyisobutylene having a viscosity-average molecular weight of from 500,000 to 2,500,000 and an oil as main bases.

2. The formulation without scopolamine for percutaneous administration for treating disturbance in micturition of claim 1, which comprises, based on the total amount of the adhesive, 0.01 to 50 parts by weight of the medicine for treating disturbance in micturition, said adhesive containing 1 to 60 parts by weight of said low-molecular weight polyisobutylene, 0.1 to 40 parts by weight of said high-molecular weight polyisobutylene, an oil, and 5 to 50 parts by weight of a styrene-isoprene-styrene block copolymer as main bases.

3. The formulation without scopolamine for treating disturbance in micturition according to claim 1, wherein said medicine for treating disturbance in micturition is a medicine for treating urinary incontinence, a medicine for treating difficulty of micturition, a medicine for treating pollakisuria, or a medicine for treating pain on micturition.

4. The formulation without scopolamine for treating disturbance in micturition according to claim 1, wherein said medicine for treating disturbance in micturition is a medicine for treating urinary incontinence.

5. The formulation without scopolamine for treating disturbance in micturition according to claim 1, wherein said oil is selected from the group consisting of liquid paraffin having a viscosity of 5 to 100 mm$^2$/s, natural squalene, synthetic squalene, squalane, and mixtures thereof.

6. The formulation without scopolamine for treating disturbance in micturition according to claim 1, which further comprises a transdermal enhancer.

7. A formulation without scopolamine for percutaneous administration for treating disturbance in micturition according to claim 3, wherein the medicine for treating urinary incontinence, difficulty of micturition, pollakisuria, or pain on micturition is selected from the group consisting of bethanechol, distigmine, prostaglandins (PGE$_1$, PGE$_2$, PGF$_2\alpha$), propanthelin, oxybutynin, terodiline, flavoxate, propiverine, vamicamide, urapidil, tiropramide, alfuzosin, imipramine, amitriptyne, ethylphenylephrine, ephedrine, phenoxybenzamine, prazosin, bunazocin, diazepam, dantrolene, clenbuterol, terazosin, inaperisone, terflavoxate, naftopidil, and a pharmaceutically acceptable salt thereof.

8. The formulation without scopolamine for percutaneous administration for treating disturbance in micturition according to claim 1, wherein said medicine is oxybutynin or a pharmaceutically acceptable salt thereof.

* * * * *